United States Patent
Stock et al.

(10) Patent No.: US 11,181,472 B2
(45) Date of Patent: Nov. 23, 2021

(54) ALCOHOL DETECTION DEVICE WITH REDUNDANT MEASURING CHANNELS AND METHOD FOR DETECTING ALCOHOL IN BREATHING AIR

(71) Applicant: Dräger Safety AG & Co. KGaA, Lübeck (DE)

(72) Inventors: Burkhard Stock, Carlow (DE); Malte Baesler, Bargteheide (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 0 days.

(21) Appl. No.: 16/723,045

(22) Filed: Dec. 20, 2019

(65) Prior Publication Data

US 2020/0200676 A1   Jun. 25, 2020

(30) Foreign Application Priority Data

Dec. 21, 2018 (DE) .................... 10 2018 009 981.5

(51) Int. Cl.
*G01N 21/3504* (2014.01)
*G01N 33/00* (2006.01)

(52) U.S. Cl.
CPC ..... *G01N 21/3504* (2013.01); *G01N 33/0036* (2013.01); *G01N 2201/068* (2013.01)

(58) Field of Classification Search
CPC ........... G01N 21/3504; G01N 33/0036; G01N 2201/068
See application file for complete search history.

(56) References Cited

U.S. PATENT DOCUMENTS

| 5,515,859 | A  | * | 5/1996  | Paz ........................ | A61B 5/083 250/339.1 |
|-----------|----|---|---------|------------------------------|----------------------|
| 6,464,941 | B1 |   | 10/2002 | Diekmann                     |                      |
| 2002/0003266 | A1 |   | 1/2002  | Manning                   |                      |
| 2002/0036266 | A1 | * | 3/2002  | Dreyer ...............     | G01N 21/3504 250/345 |
| 2003/0192368 | A1 | * | 10/2003 | Kempe ..............       | G01N 21/3504 73/61.41 |

(Continued)

FOREIGN PATENT DOCUMENTS

DE  19607062 A1  8/1997
DE  19619673 C2  11/1997

(Continued)

OTHER PUBLICATIONS

Tarsitano, "Multilaser Herriott cell for planetary tunable laser spectrometers" Applied Optics, Oct. 1, 2007.

(Continued)

*Primary Examiner* — Jamil Ahmed
(74) *Attorney, Agent, or Firm* — McGlew and Tuttle, P.C.

(57) ABSTRACT

A device and a process detects alcohol in a gas sample, especially in an exhaled breath sample. A measuring chamber (2) receives the gas sample to be tested. Two IR radiation sources (7, 11) are configured to transmit an IR beam each into the measuring chamber (2). Two IR detectors (9, 13) generate a measured value each depending on an incident IR beam. An analysis unit (10) automatically makes a decision on whether or not the gas sample contains alcohol, doing so depending on the two measured values from the two IR detectors (9, 13).

20 Claims, 3 Drawing Sheets

(56) References Cited

U.S. PATENT DOCUMENTS

| | | | |
|---|---|---|---|
| 2005/0247878 A1* | 11/2005 | Baschant | G01N 21/3504 250/343 |
| 2015/0300948 A1 | 10/2015 | Buchtal et al. | |
| 2017/0268992 A1 | 9/2017 | Schmidt-Kaeding | |
| 2017/0296109 A1 | 10/2017 | Morley et al. | |
| 2018/0116555 A1 | 5/2018 | Dreyer et al. | |

FOREIGN PATENT DOCUMENTS

| | | |
|---|---|---|
| DE | 102006018970 B3 | 5/2007 |
| DE | 102011106410 B3 | 8/2012 |

OTHER PUBLICATIONS

Schoknecht, "Beweissicherheit der Atemalkoholanalyse" Unfall- und Sicherheitsforschung Straßbenverkehr, 1992.

* cited by examiner

ALCOHOL DETECTION DEVICE WITH REDUNDANT MEASURING CHANNELS AND METHOD FOR DETECTING ALCOHOL IN BREATHING AIR

CROSS REFERENCE TO RELATED APPLICATIONS

This application claims the benefit of priority under 35 U.S.C. § 119 of German Application 10 2018 009 981.5, filed Dec. 21, 2018, the entire contents of which are incorporated herein by reference.

TECHNICAL FIELD

When a person has consumed alcohol, the breathing air exhaled by the person contains a certain percentage of alcohol (ethanol). An alcohol detection device automatically recognizes whether a person (the test subject) has consumed alcohol and this has not yet decomposed and the test subject is still under the influence of alcohol. The test subject introduces a breath sample into the alcohol detection device, and the alcohol detection device automatically tests the breath sample for alcohol.

TECHNICAL BACKGROUND

Such an alcohol detection device typically comprises a measuring chamber, into which a gas sample containing breathing air exhaled by the test subject is introduced, and a sensor system. For example, the test subject blows into a mouthpiece, which is in fluidic connection with the measuring chamber.

The alcohol detection device shall at least detect and display whether or not the introduced breath sample has an alcohol content above a predefined limit, for example, above a predefined detection limit. If alcohol is detected, the test subject is preferably subjected to closer testing. It is also possible that the alcohol detection device measures and displays an alcohol concentration in the breathing air.

Various manners in which an alcohol detection device measures the alcohol content in a gas sample, while this gas sample is present in the measuring chamber, have become known. A principle that has become known is that an infrared beam (IR beam) is emitted into the measuring chamber, it passes through the gas sample in the measuring chamber, and reaches a photosensor, which generates a measured value as a function of the intensity of the IR beam reaching the photosensor. Alcohol present in the gas sample causes an attenuation and therefore reduces the light intensity in a certain wavelength range, which leads to a change in the measured value compared to an alcohol-free gas sample. The detection device according to the present invention likewise utilizes this principle.

SUMMARY

A basic object of the present invention is to provide a device and a process for detecting alcohol in a gas sample, which operates with a higher reliability than prior-art devices and processes.

The device according to the present invention comprises
a measuring chamber,
a first IR radiation source and a second IR radiation source,
a first IR detector and a second IR detector, as well as
a signal-processing analysis unit.

The measuring chamber is capable of receiving a gas sample, especially a gas sample to be tested for alcohol or another gas sample or also a reference gas sample free from alcohol or a reference gas sample containing alcohol.

Each IR radiation source is capable of emitting an IR beam each into the measuring chamber. Each IR detector is capable of generating a measured value each, doing so independently from an incident IR beam, preferably depending on the light intensity of an incident IR beam.

The device according to the present invention is configured to be operated as follows, and the process according to the present invention comprises the following steps:

A gas sample to be tested for alcohol is introduced into the measuring chamber.

While the gas sample to be tested is present in the measuring chamber, the first IR radiation source and the second IR radiation source emit each a respective IR beam into the measuring chamber.

The IR beam from the IR radiation source passes through the measuring chamber and thus also through the gas sample to be tested in the measuring chamber and reaches the first IR detector.

The IR beam from the second IR radiation source passes through the measuring chamber and thus also through the gas sample to be tested in the measuring chamber and reaches the second IR detector.

The first IR detector generates a first measured value independently from the IR beam reaching it.

The second IR detector generates a second measured value independently from the IR beam reaching it.

The analysis unit automatically decides whether or not the gas sample in the measuring chamber contains alcohol. The analysis unit uses for this decision at least the two measured values from the two IR sensors, which were generated while the gas sample to be tested was present in the measuring chamber.

The measuring chamber encloses the gas sample to be tested and isolates the gas sample from the ambient air.

A detection device with IR radiation sources and IR detectors requires, contrary to, e.g., a detection device with semiconductor sensors, no high-power heater in order to bring a semiconductor to a reaction temperature, and it is in many cases more reliable than a detection device with an electrochemical sensor. In addition, an IR detection device according to the present invention does not use any chemical, which can react with alcohol and indicates alcohol by the reaction. Having to use such a chemical has the drawbacks that the chemical needs to be replaced, as a rule, from time to time and/or may be hazardous.

The present invention provides two detection units operating independently from one another, namely, a first detection unit with the first IR radiation source and with the first IR detector as well as a second detection unit with the second IR radiation source and with the second IR detector. Each detection unit yields at least one measured value each. The analysis unit is in a data connection with these two detection units and receives both measured values. Since two detection units operating independently from one another are used according to the present invention, the reliability of a result delivered by the detection device increases compared to a detection device that has only a single detection unit.

It is made possible that the analysis unit compares to one another the two or at least two measured values from the two detection units—or two signals, which depend on the measured values and are each an indicator of the alcohol concentration in the gas sample—and not only makes the decision, depending on the comparison, on whether or not the gas sample contains alcohol, but it additionally decides whether or not this result is sufficiently reliable. It is made possible that even though the two detection units have equal sensitivity for ethanol, they have different sensitivities to at least one other substance, which may occur in the gas sample. The detection device is capable of distinguishing alcohol from this other substance in the gas sample in this case.

Furthermore, a redundancy is provided thanks to the two detection units. If one IR radiation source or one IR detector fails, the detection device can still always test a gas sample in the measuring chamber.

Thanks to the two redundant detection units, the detection devices deliver in many cases a conclusive result and/or a result that is valid for legal purposes.

These two detection units use according to the present invention the same measuring chamber. As a result, the necessity to split a gas sample to be tested between two measuring chambers or even to provide two gas samples is eliminated. Because the same gas sample is tested in the same measuring chamber, the measured values or signals of the two detection units can be compared to one another with a greater reliability than in the case in which two detection units with two different measuring chambers were used. In addition, the feature according to the present invention that the same measuring chamber is used for both detection units makes it possible to configure the detection device as a more compact device and as a device requiring less space compared to a detection device comprising two separate measuring chambers. This feature makes it easier, in particular, to provide a detection device that can be carried by a person in his hand and is nevertheless reliable.

According to the present invention, the detection device is capable of deciding automatically whether or not a gas sample to be tested in the measuring chamber contains alcohol. In one embodiment, the detection device is additionally capable of quantitatively determining the content or the concentration of alcohol (ethanol) in this gas sample.

The two detection units and especially the two IR detectors preferably work independently from one another. The results of one IR detector do not influence the results of the other IR detector. The detection device preferably bundles an IR beam from an IR radiation source such that this IR beam reaches exclusively or at least essentially only the IR detector associated with this IR radiation source and it does not reach the other IR detector or another IR detector. The IR beam emitted by the first IR radiation source preferably reaches exclusively or almost exclusively the first IR detector, and the IR beam emitted by the second IR radiation source reaches exclusively or almost exclusively the second IR detector. The two beam paths of the two IR beams do not ideally influence each other.

The measuring chamber preferably has a mirror symmetrical configuration in relation to the central plane. The first detection unit with the first IR radiation source and with the first IR detector is preferably located on one side of this central plane, and the second detection unit with the second IR radiation source and with the second IR detector is located on the other side. This configuration makes possible an especially simple construction.

It is possible that the two IR detectors have a similar configuration and have a similar spectral sensitivity. By contrast, each IR detector comprises a wavelength filter and the photosensor proper in a preferred embodiment. Each wavelength filter is capable of filtering an incident IR beam such that a partial IR beam passes through this wavelength filter in a certain wavelength range and reaches the photosensor. Components of the IR beam reaching the filter outside this wavelength range are filtered out or at least attenuated. The photosensor generates, depending on an incident partial IR beam, a measured value, preferably as a function of the light intensity of the incident partial IR beam.

The first wavelength filter, which belongs to the first IR detector, preferably allows a partial IR beam to pass through in a first wavelength range. The second wavelength filter, which belongs to the second IR detector, allows a partial IR beam to pass through in a second wavelength range. These two wavelength ranges preferably differ from one another. Each wavelength range of a wavelength filter preferably comprises a partial range, which is absorbed sufficiently strongly by ethanol in the air. The two wavelength ranges can be set such that even though the two detection units have equal sensitivity for ethanol, i.e., they yield approximately the same measured values in the case of alcohol in the gas sample as long as the alcohol concentration is in a predefined range, they have different sensitivities for at least one other substance, which may likewise be present in the gas sample and hence in the measuring chamber. Further, this embodiment reduces the sensitivity of the detection device to substances that could influence a result of the detection device, and could especially mimic or else hide alcohol.

This embodiment with the wavelength filters makes it possible in an especially simple manner to provide two similar photosensors for the two IR detectors. This reduces the variance. The different sensitivities can be obtained exclusively by different or actuatable wavelength filters and/or by the measured values of the IR detectors being analyzed by the analysis unit in a suitable manner.

In one embodiment, at least one wavelength filter, preferably each wavelength filter, is operated optionally in a first mode or in a second mode. The wavelength filter allows a partial IR beam in the first wavelength range to pass through in the first mode, and a partial IR range in the second wavelength range in the second mode. This embodiment makes it possible optionally to operate the first wavelength filter in the first mode and the second wavelength filter in the second mode or the first wavelength filter in the second mode and the second wavelength filter in the first mode.

In one embodiment of this configuration, the wavelength filter or each wavelength filter, which can be operated in two modes, has a first segment, which allows a partial IR beam to pass through in the first wavelength range, and a second segment, which allows a partial IR beam to pass through in the second wavelength range. The wavelength filter can be moved relative to the associated photosensor, so that an incident IR beam is filtered by the first segment or by the second segment depending on the position of the wavelength filter. The wavelength filter is arranged, e.g., rotatably or linearly displaceably. In another embodiment of this configuration, the wavelength filter can be switched by correspondingly adjusting an applied control voltage.

It is made possible that when testing a gas sample in the measuring chamber, each IR detector generates, one after another, two measured values each, namely, a first measured value while the wavelength filter of this IR detector is in the first mode, and a second measured value while the wavelength filter of this IR detector is in the second mode. The analysis unit makes the decision on whether or not the gas sample contains alcohol, depending at least on the two first measured values and on the two second measured values. This embodiment leads to a further increase in the reliability of the detection devices. Further, this embodiment makes it possible in an especially simple manner to provide two similar IR detectors.

It is possible that the detection device switches the wavelength filter or each wavelength filter automatically over from one mode into the other mode while a gas sample to be tested is present in the measuring chamber. It is also possible that a corresponding user unit triggers the step to switch the wavelength filter or each wavelength filter.

According to the present invention, an IR beam passes through the measuring chamber from the first IR radiation source and reaches the first IR detector. An IR beam from the second IR radiation source likewise passes through the measuring chamber and reaches the second IR detector. It is possible that these IR beams reach the respective IR detector directly. By contrast, each IR beam is preferably reflected over its path in the measuring chamber from the respective IR radiation source to the respective IR detector at least once and preferably several times. This embodiment increases the length of the beam path that is traveled by an IR beam on its path from the IR radiation source to the IR detector, doing so preferably several times. While the dimension of the measuring chamber is the same, this leads to a longer section, over which the gas sample to be tested can influence the light intensity (greater absorption length). Furthermore, each IR beam passes through a larger portion of the volume of the measuring chamber, so that a result of the detection device has a higher reliability even when alcohol may be distributed unevenly in the measuring chamber, compared to an embodiment of the detection device without mirror.

The detection device comprises according to the present invention two detection units, each comprising an IR radiation source and an IR detector. The two IR radiation sources emit an IR beam each into the same measuring chamber, and an IR beam each from the same measuring chamber reaches the two IR detectors. The embodiment with the mirrors has the further advantage that the same mirror or the same arrangement with a plurality of mirrors is used for both detection units. It is not necessary to provide a separate mirror arrangement for each detection unit. This reduces the number of necessary components and hence the dimension and/or the weight of the detection device, without reducing the reliability thereof.

According to the present invention, the two IR beams pass through the same measuring chamber. This has especially the following advantage over a conceivable embodiment with two measuring chambers, through which a respective IR beam passes. Either is the detection device with two measuring chambers markedly larger than the detection device according to the present invention with a measuring chamber used by both detection units, or each of the two measuring chambers is smaller than the measuring chamber of the detection device according to the present invention. Each IR beam can now achieve only a shorter absorption length than the IR beams of the detection device according to the present invention. In addition, a detection device according to the present invention produces in many cases a higher light intensity of the emitted IR beams than the other detection device at equal energy consumption.

At least one mirror each is preferably arranged at two walls of the measuring chamber, so that the measuring chamber has at least two mirrors. An IR beam is therefore preferably mirrored at least twice, especially preferably four to eight times, and especially six times, on its way from an IR radiation source to an IR detector. The two walls with the two mirrors and hence the two mirrors are preferably located opposite each other, so that a gas sample in the measuring chamber is located between these two mirrors. The absorption length is preferably between 350 mm and 450 mm and especially preferably about 400 mm. In the case in which the two walls with the mirrors are located opposite each other, the distance between the two mirrors is preferably between 50 mm and 60 mm. How often an IR beam is reflected depends on the distance between the mirrors.

Preferably at least one mirror is configured as a concave mirror and especially preferably both mirrors are configured as concave mirrors. This configuration deflects an incident IR beam more strongly towards the center of the measuring chamber compared to a planar mirror. This makes it easier to obtain a desired absorption length in a more reliable manner. How often an IR beam is reflected depends, in addition, on the focal lengths of the two concave mirrors.

An IR radiation source each is associated according to the present invention with each IR detector. An IR beam from this associated IR radiation source reaches the IR detector. The IR beam is preferably reflected on its way from the IR radiation source to the IR detector at a mirror at least once, especially preferably at least once at a first mirror and at least once at a second mirror, the two mirrors being preferably located opposite each other. In one embodiment, the IR detector and the IR radiation source are arranged on two mutually opposite walls with one respective mirror each, so that the measuring chamber and hence the gas sample in the measuring chamber are located between the mirrors. An IR beam is consequently reflected on its way from the IR radiation source to the IR detector preferably at least twice, preferably four times or even six times. The absorption length now equals three times, five times or even seven times the distance between the two mirrors located opposite each other.

In one embodiment, the two IR radiation sources are arranged at two mutually opposite walls of the measuring chamber. This embodiment reduces in some cases the risk that the two IR radiation sources would mutually influence each other in an undesired manner. In another embodiment, the two IR radiation sources are arranged on the same wall of the measuring chamber, preferably at spaced locations from one another. This embodiment reduces in many cases the length of lines between the analysis unit and the two IR radiation sources.

The two IR detectors are correspondingly arranged in one embodiment on two mutually opposite walls of the measuring chamber. In another embodiment, the two IR detectors are arranged on the same wall of the measuring chamber, preferably at spaced locations from one another. In a variant of this embodiment, the two IR detectors are arranged on the same first wall of the measuring chamber and the two IR radiation sources on the same second wall of the measuring chamber, the first wall and the second wall being located opposite each other, so that a gas sample in the measuring chamber is located between these two walls.

In a variant of this embodiment, the two IR radiation sources and/or the two IR detectors are integrated in mirrors on the walls of the measuring chamber. For example, the two IR radiation sources are integrated in one mirror, and the two IR detectors are integrated in a mirror located opposite thereto.

In a variant of the embodiment with the mirrors, the measuring chamber is configured as a Herriott cell with two mutually opposite concave mirrors and is mirror-symmetrical in relation to a central plane. The two focal points of the two mutually opposite concave mirrors are preferably located on this central pane. This central plane thus provides a coinciding optical axis of the two concave mirrors.

The measuring chamber preferably gas a gastight configuration, so that the testing of the gas sample is not distorted by gas that additionally enters the measuring chamber or by gas of the gas sample, which gas is escaping from the measuring chamber. The gas sample to be tested can preferably enter the measuring chamber exclusively through an inlet. The gas sample to be tested can preferably leave the measuring chamber exclusively through an outlet. This outlet is preferably secured by a non-return valve or another, correspondingly suitable element, so that even though gas can leave the measuring chamber through the outlet, no gas, especially no ambient air, can enter the measuring chamber through the outlet. It is possible that the same opening in a wall of the measuring chamber belongs to both the inlet and the outlet.

The maximum dimension of the measuring chamber is preferably between 80 mm and 120 mm and it equals especially about 100 mm.

The measuring chamber is capable according to the present invention of receiving a gas sample to be tested for alcohol. This gas sample is given, for example, by a test subject, especially by exhaling, and the test subject transfers the gas sample into the measuring chamber himself. It is also possible that the detection device has a delivery unit, which delivers the gas sample to be tested and/or a reference gas sample into the measuring chamber.

In one embodiment, the detection device is capable of flushing the measuring chamber, especially of removing an already tested gas sample from the measuring chamber and of replacing it with a reference gas sample, which contains no alcohol or else which contains alcohol at a known concentration. It is possible that the detection device automatically replaces the tested gas sample or the gas already present in the measuring chamber for a rather long time with a new gas sample to be tested or else with a reference gas sample, for example, after each testing of a gas sample or at predefined time intervals. It is also possible that the detection device replaces the tested gas sample with a reference gas sample as a response to a corresponding user input.

It is possible that this reference gas sample is fed by an external delivery unit or, for example, from a compressed air cylinder.

In a preferred configuration of this embodiment, the detection device comprises, by contrast, a delivery unit of its own, especially a pump, which is capable of delivering a reference gas sample into the measuring chamber or from the measuring chamber, as well as an outlet, through which the gas sample to be tested can escape from the measuring chamber. The analysis unit preferably actuates this delivery unit, and the delivery unit remains switched on and delivers gas as long as the measuring chamber is filled exclusively with the reference gas sample. In one configuration, the analysis unit switches on the delivery unit for a predefined time period and then switches it off. In another embodiment, a flow sensor at the inlet measures the volume flow, and the analysis unit calculates the quantity of gas that has been delivered so far by the delivery unit into the measuring chamber (integration over the volume flow) on the basis of measured values of the flow sensor, and it switches the delivery unit off again when this hitherto delivered quantity delivered up to this point has reached or exceeded the volume of the measuring chamber, for example, after at least 1 L of gas has been delivered into the measuring chamber. The flow sensor can also measure the flow of gas out of the measuring chamber.

The reference gas sample may be a gas sample that is free from alcohol. It is possible that such an alcohol-free gas sample is taken from the ambient air. A filter, which filters particles out of the air flowing in or from the introduced breath sample, may be provided in the inlet into the measuring chamber. A reference gas sample, which contains a known concentration of alcohol, is fed, for example, during an optional calibration or adjustment of the detection device, which will be described as an example below.

The embodiment in which the detection device can replace a tested gas sample with an alcohol-free reference gas sample in the measuring chamber makes possible the following mode of operation of the detection device according to the present invention:

When the measuring chamber is filled with the alcohol-free gas sample, each IR radiation source emits an IR beam each into the measuring chamber. Each IR detector generates a measured value. The light intensity of this IR beam is not reduced by alcohol in the gas sample. The measured value from the first IR detector is used therefore as the first zero measured value, and the measured value from the second IR detector as the second zero measured value.

The measuring chamber is then filled with the gas sample to be tested. Each IR radiation source emits again an IR beam into the measuring chamber. Each IR detector generates a measured value. At least when the gas sample to be tested contains alcohol, one measured value is lower, as a rule, than the corresponding zero measured value from the same IR detector, because alcohol absorbs and hence attenuates IR light.

It is also possible that the gas sample to be tested is first introduced into the measuring chamber and the alcohol-free gas sample is then introduced later, and the measured values are generated first and the zero measured values are then generated thereafter.

Depending on the first zero measured value and on the first measured value (measured value that has been generated by the first IR detector, while the measuring chamber is filled with the gas sample to be tested), the analysis unit generates a first signal. The analysis unit generates a second signal depending on the second zero measured value and the second measured value. Each signal is an indicator of the concentration of ethanol in the gas sample. The analysis unit compares these two signals to one another and generates a test result depending on the result of the comparison.

Because the detection device according to the present invention comprises two preferably mutually independently operating detection units, but these two detection units use the same measuring chamber, only one measuring chamber needs to be emptied. This is a further advantage compared with a detection device with two separate measuring chambers.

Each IR beam passes through a beam path on its way from an IR radiation source to the associated IR detector and is absorbed more or less strongly by gas in the measuring chamber over its beam path. Therefore, each IR beam achieves one absorption length. The detection device is preferably configured such that the two IR beams ideally achieve the same absorption length. The actually achieved absorption lengths may, however, differ from one another in practice due, for example, to inaccuracies in manufacture and assembly. The procedure just described, according to which the measuring chamber is emptied before or after each test, reduces the influence of different absorption lengths on the measurements.

This embodiment may be combined with the embodiment in which the two IR detectors do have the same sensitivity to ethanol in the gas sample, but they have different sensitivities to at least one additional possible substance. If the two signals agree within a tolerance, the measurement result is reliable, both when alcohol is detected and also when the non-existence of alcohol in the gas sample is detected. If the two signals differ from one another by more than the tolerance, the analysis unit preferably yields at least one of the following results depending on the two signals:

The gas sample contains at least one additional substance, which attenuates the light intensity of one IR beam more strongly than it does the light intensity of the other IR beam.

The measuring chamber is exposed to an interfering electromagnetic radiation from the outside, which is superimposed to the IR beams of the two IR radiation sources.

One IR radiation source and/or one IR detector and/or one data connection has failed.

The detection device is often incapable in these situations of distinguishing alcohol from other substances in the measuring chamber with a sufficient reliability. It is possible in some cases to flush the measuring chamber by introducing an alcohol-free gas sample into the measuring chamber, then introducing a gas sample into the measuring chamber and testing this, in which case no interfering substances will be present in the measuring chamber any longer.

The embodiment in which an alcohol-free reference gas sample is regularly introduced into the measuring chamber, for example, after or also before each testing of a gas sample, and two zero measured values are generated, has especially the following advantage: If a property of an IR voltage source or of an IR detector changes gradually (e.g., based on parameter drift or declining voltage supply or contamination), this gradual change can be compensated by calculation and at a low effort. It is sufficient for the properties to remain constant during the time period during which the reference gas sample and thereafter or before the gas sample to be tested are present in the measuring chamber. This usually happens because this time period is in the range of less than one minute or in the range of a few minutes.

In one embodiment, the two signals, which the analysis unit calculates as a function of the two measured values and of the two zero measured values, depend on the absolute attenuation or the percentage of the attenuation, which is produced in the light intensity of the respective IR beam by alcohol or another substance in the gas sample to be tested.

In a variant of this embodiment, the two signals additionally depend on two calibration factors. These calibration factors are preferably predefined or are generated in advance. In the case of this advance generation, the two IR detectors generate, on the one hand, as was just described, two zero measured values, while an alcohol-free reference gas sample is present in the measuring chamber. In addition, an additional reference gas sample is introduced into the measuring chamber, and this additional reference gas sample contains alcohol, preferably at a concentration that typically occurs in the exhaled breathing air of a person who consumed alcohol. The two IR detectors generate two reference measured values, while the measuring chamber is filled with this alcohol-containing reference gas sample.

To test a gas sample for alcohol later, the analysis unit generates, as was described above, two signals, which depend on the two measured values and the two zero measured values as well as the two calibration factors. The analysis unit applies here a stored calculation rule, which contains the two calibration factors. The two calibration factors are used during the calibration such that the calculation rule, applied to the first reference measured value, to the first zero measured value and to the first calibration factor, yields the same signal as when applied to the second reference measured value, to the second zero measured value and to the second calibration factor. As a result, the two IR detectors have the same sensitivity for ethanol. As was described above, two different wavelength filters are thus preferably used.

This configuration with the calibration factors and preferably with the different wavelength filters leads to a further reduction of the influence of possibly different absorption lengths of the two IR beams. It becomes possible in some cases to predefine a greater manufacturing and assembly tolerance during the manufacture of the detection device compared to an embodiment in which the two absorption lengths exactly agree.

According to the present invention, the detection device comprises two detection units with a respective IR radiation source and with an IR detector each. It is possible that the detection device comprises three or even more detection units with a respective IR radiation source and an IR detector each, which use all the same measuring chamber and optionally the same mirror arrangement, and the IR radiation sources and the IR detectors may each be able to have similar configurations.

The detection device according to the present invention can be used for a test to determine whether or not a breathing air from a test subject contains alcohol. The detection device may also be used for other applications, in which a gas sample is to be tested to determine whether it contains alcohol, e.g., to test whether a container, which contains an alcohol-containing liquid, is tight or whether alcohol vapor escapes.

The present invention will be described below on the basis of an exemplary embodiment.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Referring to the drawings, the device according to the present invention is capable of detecting whether or not alcohol is present in the breathing air exhaled by a test subject. The device is capable, furthermore, of deciding whether or not the alcohol content in the exhaled breathing air is above a predefined threshold, e.g., a detection threshold or a legally stipulated threshold. It is optionally even capable of determining and outputting the alcohol content in a breathing air quantitatively.

The device according to the present invention is preferably configured as a device that can be carried in the hand by a person and can be used, for example, to test for alcohol drivers operating road vehicles, rail-borne vehicles, watercraft, aircraft or even persons who wish to or shall enter a certain area or a certain plant.

Figure 1:
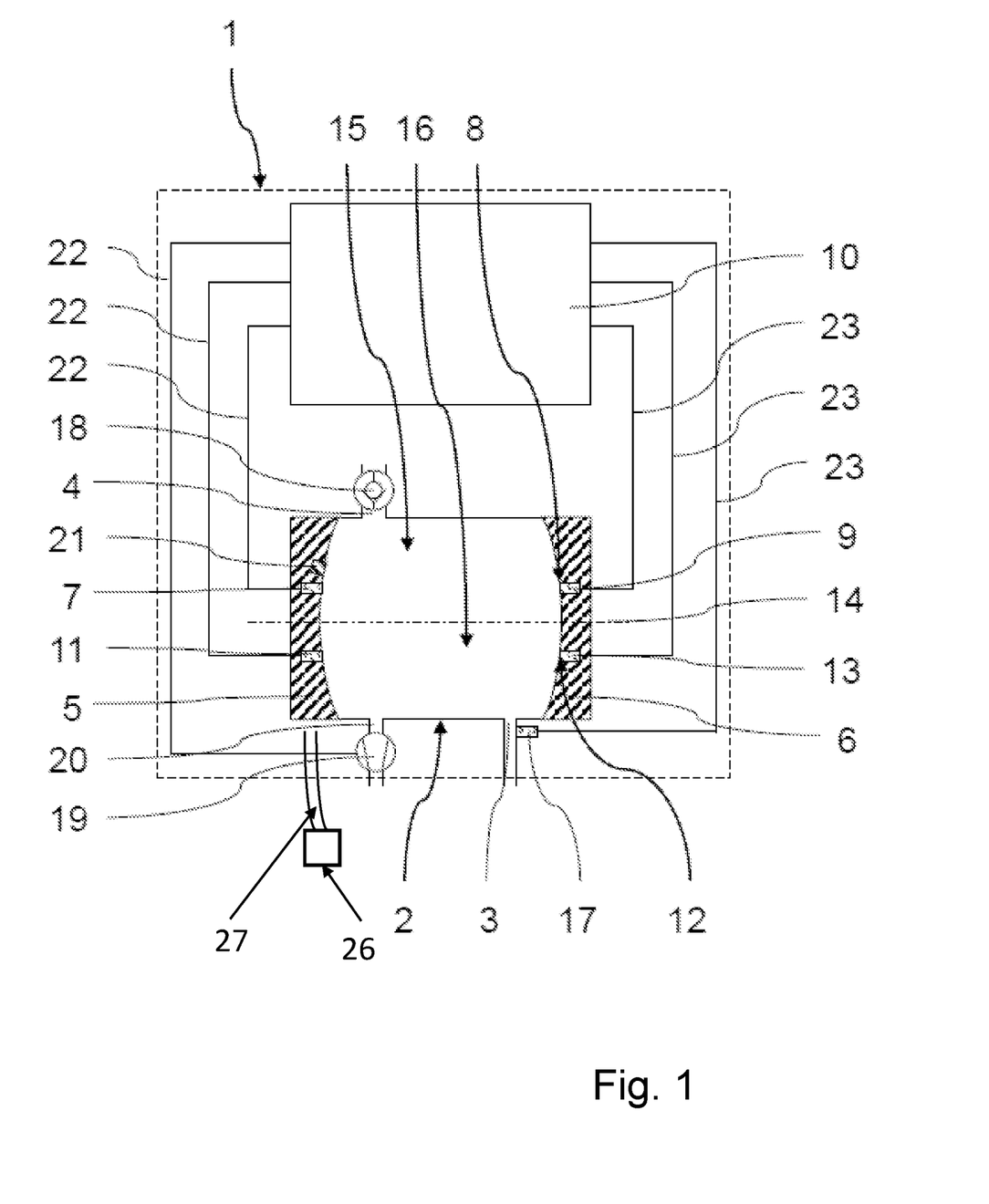
FIG. 1 is a schematic view showing a preferred embodiment of a detection device according to the present invention.

FIG. 1 schematically shows a preferred embodiment of a detection device according to the present invention. The detection device comprises a housing ("cuvette body") 1, in which a measuring chamber ("cuvette") 2 having an inlet 3 and an outlet 4 is arranged. The inlet 3 is preferably in fluidic communication with an input device, for example, with a mouthpiece or with a funnel, into which a person can blow breathing air. Gas, especially exhaled breathing air, can flow through the inlet 3 into the measuring chamber 2 and flow out of the measuring chamber 2 through the outlet 4. FIG. 1 schematically shows a mouthpiece 26, which is in fluidic connection with the inlet 3 via a flexible tube 27. In one embodiment, a closure, not shown, e.g., a cap, is capable of closing the inlet 3 or the mouthpiece 26 or the flexible tube 27. An optional flow sensor 17 measures the volume flow, which flows through the inlet 3 into the measuring chamber 2. An optional non-return valve 18 prevents ambient air from flowing through the outlet 4 into the measuring chamber 2 and from being able to distort the measurement result. By contrast, the non-return valve 18 makes it possible for gas to flow out of the measuring chamber 2 through the outlet 4.

An optional filter, not shown, at the inlet 3 prevents water droplets, dust particles or other interfering particles from entering the measuring chamber 2. A heater, not shown, preferably maintains the air temperature in the measuring chamber 2 at at least 40° C. This reduces the risk of condensation of water on the wall of the measuring chamber 2 and the condensed water from distorting measurement results or from being able to damage a component.

An output unit, not shown, outputs a test result in a form perceptible by a person, especially optically and/or acoustically. What is outputted is at least whether or not the breathing air contains alcohol at a concentration above a predefined threshold, e.g., above a detection limit or above a legally stipulated threshold. It is also possible that the output unit outputs a measured value pertaining to the measured alcohol concentration.

An optional flushing outlet 20 with a pump 19 is arranged at a spaced location from the inlet 3. In a cleansing mode of the detection device, the pump 19 is capable of drawing fluid from the measuring chamber 2, especially after a person has blown breathing air into the measuring chamber 2 and the detection device has automatically tested this breathing air. Alcohol-free ambient air can flow through the inlet 3 into the measuring chamber 2 and it replaces the tested gas sample. As a result, the detection device can be prepared for a new use. It is also possible that the pump 19 delivers an alcohol-containing reference gas sample through the inlet 3 into the measuring chamber 2.

Figure 2:
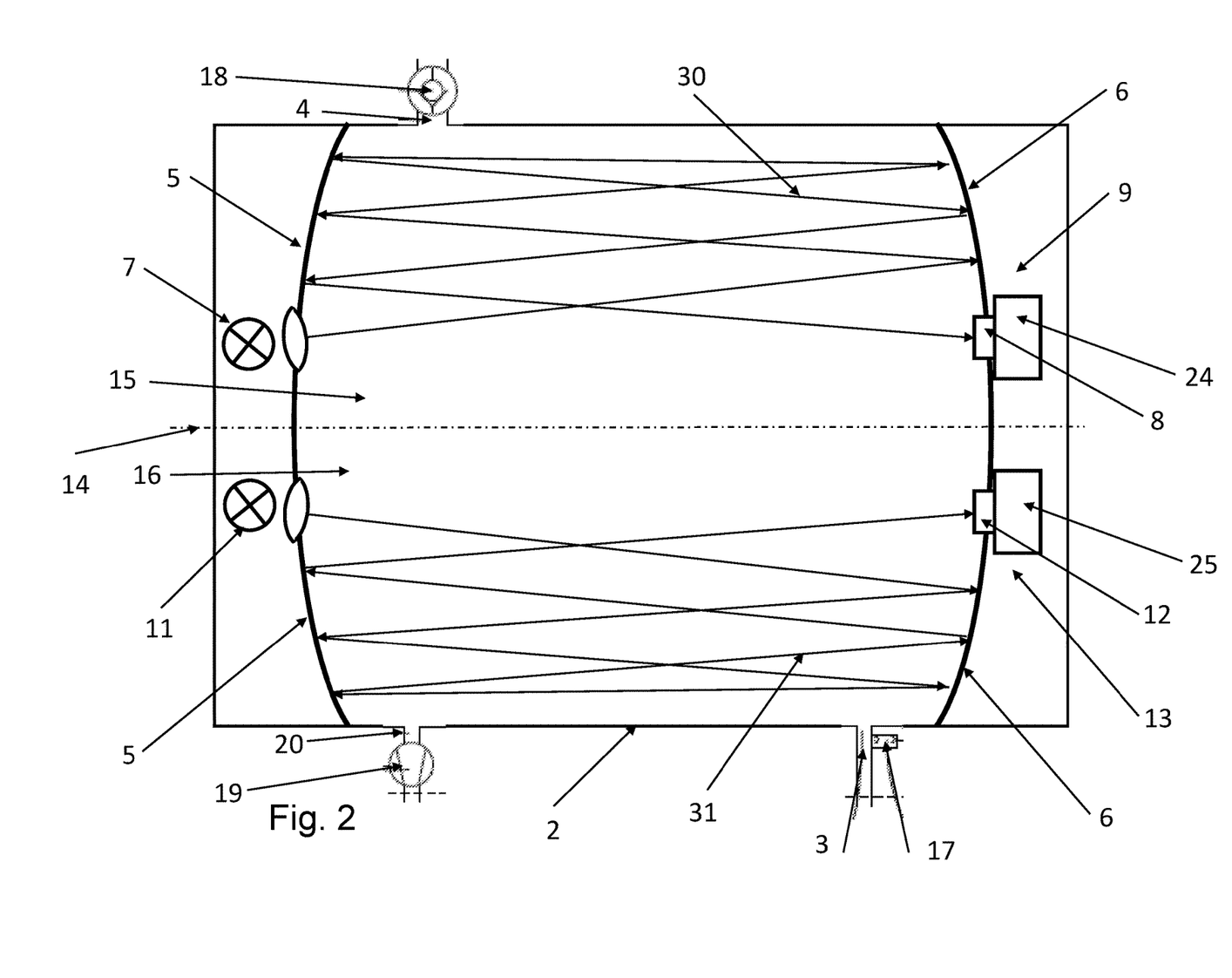
FIG. 2 is a schematic view showing a measuring chamber of the detection device according to FIG. 1 and two exemplary beam paths for the two IR beams.

FIG. 2 shows the measuring chamber 2 in detail. The measuring chamber 2 is symmetrical in the exemplary embodiment in relation to a plane of symmetry, which is at right angles to the drawing planes of FIG. 1 through FIG. 3. This plane of symmetry 14 divides the measuring chamber 2 into a first half 15 and a second half 16, which are mirror-symmetrical in relation to one another. A first detection unit, which comprises the first IR radiation source 7 and the first IR detector 9, is thus arranged in the first half 15. A second detection unit, which comprises the second IR radiation source 9 and the second IR detector 13, is arranged in the second half 16.

The measuring chamber 2 may also have a non-symmetrical configuration.

Two mutually opposite sides of the measuring chamber 2 are formed by a respective concave mirror 5 and 6 each, namely, one side by a transmitter-side concave mirror 5 and an opposite side by a receiver-side concave mirror 6. The two concave mirrors 5, 6 preferably have equal focal length. The two focal points are preferably located ideally on the optical axis 14.

A first IR radiation source 7 and a second IR radiation source 11 are recessed into the transmitter-side concave mirror 5, the first IR radiation source 7 belonging to the first half 15 and the second IR radiation source 11 to the second half 16 of the measuring chamber 2.

A first IR detector 9 and a second IR detector 13 are recessed into the receiver-side concave mirror 6, the first IR detector 9 belonging to the first half 15 and the second IR detector 13 to the second half 16 of the measuring chamber 2. The first IR detector 9 comprises a first photosensor 24 and a first wavelength filter 8. The second IR detector 13 comprises a second photosensor 25 and a second wavelength filter 12.

A heating element, not shown, preferably maintains the interior of the measuring chamber 2 at a temperature of at least 40° C., so that water is extensively prevented from condensing on a concave mirror 5 or 6 or on a wavelength filter 8, 12.

The transmission of the first wavelength filter 8 is preferably highest in a first wavelength range, and the transmission of the second wavelength filter 12 is highest in a second wavelength range. The two wavelength ranges differ and comprise a common partial area, in which an IR beam is sufficiently attenuated by alcohol in the breathing air. For example, the first wavelength range has a maximum transmission (central wavelength) at 9.6 µm, and the second wavelength range at 9.2 µm.

The two IR detectors 9 and 13 are preferably adjusted or calibrated such that despite different wavelength ranges, they have the same sensitivity for ethanol, i.e., for alcohol in the breathing air. However, the analysis unit 10 analyzes the measured values from the two IR detectors 9 and 13 such that the two detection units have different sensitivities to other substances, which may be present in the exhaled breathing air, for example, to carbon dioxide, isopropyl alcohol, methanol or acetone. Ethanol can be distinguished in this manner especially well from another substance, which may be present in an introduced breath sample.

In a preferred embodiment, two calibration factors k1 and k2, for example, weighting factors, are determined in advance for the two detector units with the two IR detectors 9 and 13 and are used for an adjustment of the detection device. This adjustment may be repeated regularly. In one embodiment, the adjustment is carried out as follows:

The measuring chamber 2 is filled with ambient air, which is free from alcohol, for example, by the pump 19 evacuating the measuring chamber 2 and by alcohol-free ambient air flowing into the measuring chamber 2 through the inlet 3 in order to compensate the vacuum generated.

Each IR radiation source 7, 11 emits a respective IR beam into the measuring chamber 2. Each IR detector 9 and 13 measures a respective zero measured value I0_ref(1) and I0_ref(2), while the measuring chamber 2 is free from alcohol.

The measuring chamber 2 is filled with a reference gas sample, which contains alcohol, preferably at a concentration that is typical of exhaled breathing air following the consumption of alcohol.

Each IR radiation source 7, 11 emits again a respective IR beam into the measuring chamber 2. Each IR detector 9 and 13 measures a respective reference measured value I1_ref(1) and I1_ref(2), while the measuring chamber 2 is filled with the alcohol-containing reference gas sample.

The two calibration factors k1 and k2 are selected to be such that they bring about the same sensitivity of the two detection units with the two IR detectors 9 and 13.

This is carried out, for example, as follows:
The two calibration factors k1 and 2 are selected in the two equations $$C\_ref(1)=k1*[I0\_ref(1)-I1\_ref(1)]/I0\_ref(1) \text{ and}$$

$$C\_ref(2)=k2*[I0\_ref(2)-I1\_ref(2)]/I0\_ref(2).$$

to be such that C_ref(1)=C_ref(2).

It is possible to repeat this calibration at regular intervals in order to compensate in this manner gradual changes of a component of the detection device.

It is also possible that the adjustment is carried out by the two wavelength filters 8 and 12 being set correspondingly. One example of this will be described below.

In one embodiment, each wavelength filter 8 and 12 may optionally be operated in a first mode or in a second mode. During operation in the first mode, the transmission is highest in the first wavelength range, and the transmission is highest in the second wavelength range during operation in the second mode. This embodiment makes it possible to operate the first wavelength filter 8 first in the first mode and the second wavelength filter 12 in the second mode and then conversely to operate the first wavelength filter 8 in the second mode and the second wavelength filter 12 in the first mode during the testing of a breathing air. The effect of a non-ideal adjustment is compensated at least partially in this manner. In addition, it is made possible that each IR detector will deliver at least two measured values while the measuring chamber 2 is filled with a breathing air to be tested.

FIG. 2 shows an example for the beam path 30 of an IR beam, which has been emitted by the first IR radiation source 7 into the measuring chamber 2, and which is reflected multiple times by the two concave mirrors 5 and 6 and which then reaches the first IR detector 9. Furthermore, FIG. 2 shows the beam path 31 of an IR beam, which the second IR radiation source 11 has emitted into the measuring chamber 2. Each IR beam is reflected seven times in the example being shown before it reaches an IR detector 9 or 13.

Figure 3:
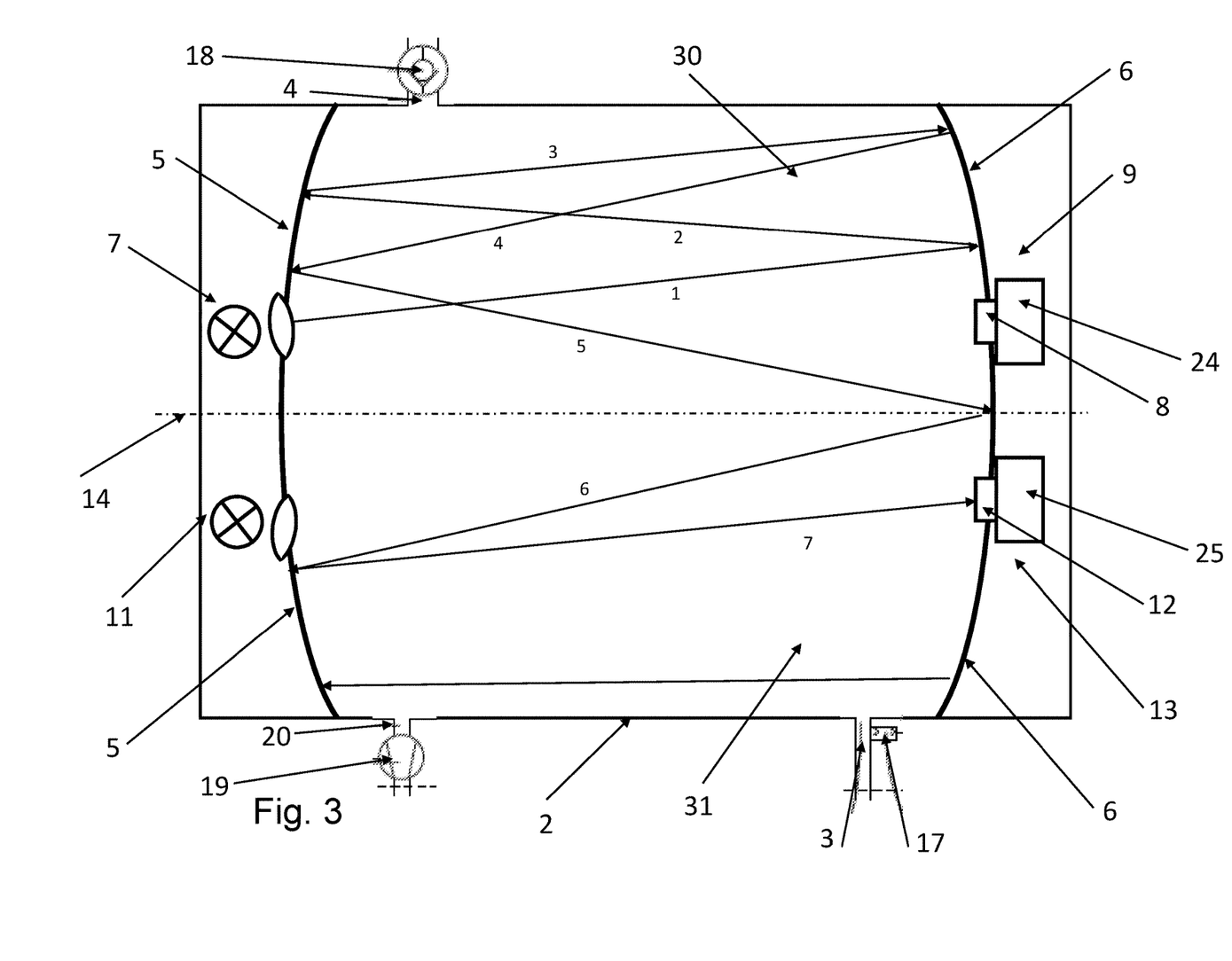
FIG. 3 is a schematic view showing the measuring chamber according to FIG. 2 with an alternative beam path for the first IR beam.

In the example according to FIG. 2, the first beam path 30 utilizes only the first half 15, and the second beam path 31 utilizes only the second half 16. FIG. 3 shows a variant in which the first beam path 30 and the second beam path 31, not shown in FIG. 3, utilizes each nearly the entire measuring chamber 2. The second beam path 31, which is mirror-symmetrical to the first beam path 30, is not shown in FIG. 3.

The maximum dimension of the measuring chamber 2 parallel to the plane of symmetry 14 is preferably 10 cm. Since each emitted IR beam is reflected several times at the two concave mirrors 5 and 6, each beam path 30 and 31 can have a length of 40 cm or more, the so-called absorption length. The absorption length equals seven times the distance between the two concave mirrors 5 and 6 in case of a six-fold reflection. Furthermore, it is made possible that the angle of incidence of an IR beam on an IR detector 9 or 13 equals at most 30°, which leads to a still sufficient aperture.

The measuring chamber 2 with the two concave mirrors 5 and 6 is preferably configured as a Herriott cell. The distance d between the two concave mirrors 5 and 6 as well as the preferably identical focal length f of the two concave mirrors 5 and 6 are selected to be such that the two IR radiation sources 7 and 11 are ideally imaged sharply and at a scale of 1:1 to the two IR detectors 9 and 13. For example, a certain focal length f of the two concave mirrors 5 and 6 and a certain f/d ratio are predefined for a sharp imaging. This results in a distance d between the two concave mirrors 5 and 6. The absorption length obtained results from the number of times an emitted IR beam is reflected. A slightly incorrect position of a concave mirror 5 or 6 therefore compromises the measurement results only slightly.

An optional first adjustable deflecting device 21 is capable of deflecting an IR beam, which has been emitted by the first IR radiation source 7, optionally to the first IR detector 9 or to the second IR detector 13 or at least of changing the direction of the IR beam. The deflecting device 21 is capable, for example, of rotating the first IR radiation source 7. An optional second deflecting device, not shown, is capable of deflecting an IR beam, which has been emitted by the second IR radiation source 11, optionally to the first IR detector 9 or to the second IR detector 13. This configuration makes it possible to operate the detection device with two IR detectors 9 and 13 even when one of the two IR radiation sources 7 or 11 has failed. In addition, a slightly incorrect position of an IR radiation source 7, 11 or of an IR detector 9, 13 can be corrected.

A data-processing analysis unit 10 is capable of transmitting control commands to the first IR radiation source 7, to the second IR radiation source 11 and to the pump 19 and optionally to a deflecting unit 21 via control lines 22. The first photosensor 24 and the second photosensor 25 generate, independently from one another, at least one respective measured value, these measured values depending each on the intensity of an IR beam 30, 31 reaching the photosensor 24 and 25, respectively. Measured values are transmitted via sensor lines 23 to the analysis unit 10 from the first photosensor 24, from the second photosensor 25 as well as from the flow sensor 17.

The detection device according to the exemplary embodiment comprises, furthermore, an energy supply unit of its own, not shown, for supplying electrical energy, for example, a set of rechargeable batteries, which make the detection device independent from a stationary supply.

The following process steps are preferably carried out in order to perform a measurement for alcohol in the breathing air of a person.

The analysis unit 10 activates the pump 19 via a control line 22.

The activated pump 19 draws gas from the measuring chamber 2. The gas drawn off is replaced by ambient air, which ambient air flows into the measuring chamber 2 through the inlet 3, in order to compensate the vacuum generated. Gas, which originates from a previous breath sample, is replaced in this manner by an alcohol-free reference gas sample. Therefore, a previous gas sample cannot distort the result.

The analysis unit 10 analyzes a measured value from the flow sensor 17 and detects the result that the volume of the ambient air drawn into the measuring chamber 2 is at least as large as the volume of the measuring chamber 2. The analysis unit 10 switches off the pump 19 again as soon as this result is detected. An alcohol-free gas sample is present now in the measuring chamber 2.

In one embodiment, a first zero measured value IOW and a second zero measured value I0(2) are read from a memory. In another embodiment, both IR radiation sources 7 and 11 emit an IR beam each, and the two IR detectors 9 and 13 measure the first zero measured value I0(1) and the second zero measured value I0(2). The two zero measured values I0(1) and I0(2) of the two IR detectors 9 and 13 are available when the gas in the measuring chamber 2 contains no alcohol. The configuration in which the two zero measured values I0(1) and I0(2) are measured again before each alcohol test has especially the following advantage: A gradual change of one component of the detection device is compensated automatically. In particular, a gradual change of an IR radiation source 7, 11 or of an IR detector 9, 13 or of the voltage source is compensated. It is sufficient for the two IR radiation sources 7, 11 and for the two IR detectors 9, 13 to remain practically unchanged during a single alcohol measurement.

A breath sample with breathing air to be tested is introduced into the measuring chamber 2 through the inlet 3. For example, a person blows into the mouthpiece 26, and the air introduced flows through the flexible tube 27 and the inlet 3 into the measuring chamber 2.

The first IR radiation source 7 emits an IR beam into the measuring chamber 2. The emitted IR beam passes through the measuring chamber 2 along the first beam path 30 and reaches the first IR detector 9.

The second IR radiation source 11 likewise emits an IR beam into the measuring chamber 2. The emitted IR beam passes through the measuring chamber 2 along the second beam path 31 and reaches the second IR detector 13.

It is possible that the IR radiation sources 7 and 11 emit an IR beam each with an overlap in time or even simultaneously. It is also possible that the two IR radiation sources 7 and 11 emit a respective IR beam one after another.

Each IR detector 9, 13 yields a measured value I1(1) and I1(2) each for the light intensity, which occurs at the photosensor 24 and 25, respectively, while the breath sample is present in the measuring chamber 2.

The analysis unit 10 calculates two signals C(1) and C(2), which represent each an indicator of the concentration of ethanol in the breath sample, depending on the two zero measured values I0(1), I0(2), and the two measured values I1(1), I1(2), for example, according to the following two formulas:

$$C(1)=k1*[I0(1)-I1(1)]/I0(1) \text{ and}$$

$$C(2)=k2*[I0(2)-I1(2)]/I0(2).$$

The calibration factors k1 and k2 are predefined or were determined in advance and are stored in a memory of the detection device. The calibration factors k1 and k2 were set, for example, as described above.

If the breath sample contains no interfering substances, the two signals C(1) and C(2) are ideally identical.

The analysis unit 10 preferably checks whether the absolute deviation or the deviation expressed as a percentage between the two signals C(1) and C(2) is below a predefined threshold. If yes, the measurement result is considered to be correct. The threshold is predefined, on the one hand, such that it is so low that the result is trustworthy in case the deviation between the two signals C(1) and C(2) is below the threshold, even if other substances and also interfering radiation have penetrated into the measuring chamber 2. On the other hand, the threshold is predefined at such a high value that unavoidable deviations between the measurement results of the two IR detectors 9 and 12 do not lead to a rejection of a correct result.

It can be recognized due to this embodiment especially that an IR radiation source 7, 11 or a first IR detector 9, 13 is defective or a beam path 30, 31 is blocked.

While specific embodiments of the invention have been shown and described in detail to illustrate the application of the principles of the invention, it will be understood that the invention may be embodied otherwise without departing from such principles.

LIST OF REFERENCE NUMBERS

1 Housing (cuvette body), which accommodates the measuring chamber 2 and the analysis unit 10
2 Gastight measuring chamber for receiving a gas sample, comprises the inlet 3, the outlet 4 and the flushing outlet 20, arranged in housing 1
3 Inlet for breathing air, connected to the mouthpiece 26
4 Outlet for breathing air
5 Transmitter-side concave mirror, forming a wall of the measuring chamber 2, accommodating the two IR radiation sources 7 and 11
6 Receiver-side concave mirror, forming a wall of the measuring chamber 2, accommodating the two IR detectors 9 and 13
7 First IR radiation source, arranged in the transmitter-side concave mirror 5
8 First wavelength filter, belonging to the first IR detector 9
9 First IR detector, arranged in the receiver-side concave mirror 6, comprising the first wavelength filter 8 and the first photosensor 24
10 Signal-processing analysis unit, controlling the two IR radiation sources 7 and 11, receiving measured values from the two photosensors 24, 25 and processing these
11 Second IR radiation source, arranged n the transmitter-side concave mirror 5
12 Second wavelength filter, belonging to the second IR detector 13
13 Second IR detector, arranged in the receiver-side concave mirror 6, comprising the second wavelength filter 12 and the second photosensor 25
14 Plane of symmetry and optical axis of the measuring chamber 2, dividing the measuring chamber 2 into the two halves 15 and 16
15 First half of the measuring chamber 2, accommodating the first IR radiation source 7 and the first IR detector 9
16 Second half of the measuring chamber 2, accommodating the second IR radiation source 11 and the second IR detector 13
17 Flow sensor at inlet 3
18 Non-return valve at outlet 4
19 Actuatable pump at the flushing outlet 20
20 Flushing outlet 20
21 First deflecting device, capable of deflecting an IR beam from the first IR radiation source 7 to the second IR detector 13, capable of rotating, for example, the first IR radiation source 7
22 Control line from the analysis unit 10
23 Sensor line to the analysis unit 10
24 First photosensor, belonging to the first IR detector 9
25 Second photosensor, belonging to the second IR detector 13
26 Mouthpiece, in fluidic connection with the inlet 3 via the flexible tube 27
27 Flexible tube, establishing a fluidic connection between the mouthpiece 26 and the inlet 3
30 Beam path of an IR beam in the measuring chamber 2 from the first IR radiation source 7 to the first IR detector 9

31 Beam path of an IR beam in the measuring chamber 2 from the second IR radiation source 11 to the second IR detector 13

The invention claimed is:

1. A device for detecting alcohol in a gas sample, the device comprising:
a measuring chamber for receiving a gas sample, wherein the gas sample is a breath sample exhaled by a test subject;
a first IR radiation source configured to emit an IR beam into the measuring chamber;
a second IR radiation source configured to emit an IR beam into the measuring chamber;
a first IR detector configured to generate at least one measured value depending on an incident IR beam;
a second IR detector configured to generate at least one measured value depending on an incident IR beam; and
a signal-processing analysis unit; wherein:
an IR beam from the first IR radiation source passes through the measuring chamber and reaches the first IR detector;
an IR beam from the second IR radiation source passes through the measuring chamber and reaches the second IR detector;
the analysis unit is configured to automatically decide whether or not a gas sample in the measuring chamber contains alcohol based on measured values that have been generated by the two IR detectors, while a gas sample to be tested is present in the measuring chamber;
the two IR detectors are arranged on two opposite walls of the measuring chamber;
a first mirror is arranged on one of the two opposite walls of the measuring chamber;
a second mirror is arranged on another one of the two opposite walls of the measuring chamber;
an IR beam emitted by the first IR radiation source is reflected by at least one of the first mirror and the second mirror at least once before the IR beam emitted by the first IR radiation source reaches the first IR detector; and
an IR beam emitted by the second IR radiation source is reflected by at least one of the first mirror and the second mirror at least once before the IR beam emitted by the second IR radiation source reaches the second IR detector.

2. A device in accordance with claim 1, wherein the two IR detectors are configured to operate independently from one another.

3. A device in accordance with claim 2, wherein:
the first IR detector comprises a first wavelength filter and a first photosensor, and the second IR detector comprises a second wavelength filter and a second photosensor;
the first wavelength filter is configured to filter an incident IR beam such that a partial IR beam in a first wavelength range passes through the first wavelength filter and reaches the first photosensor;
the second wavelength filter is configured to filter an incident IR beam such that a partial IR beam in a second wavelength range passes through the second wavelength filter and reaches the second photosensor; and
the two wavelength ranges are different from one another.

4. A device in accordance with claim 3, wherein:
at least one of the two wavelength filters is operable in a first mode or in a second mode;
the wavelength filter is configured to filter an incident IR beam in the first mode such that a partial IR beam in the first wavelength range passes through the wavelength filter and
the wavelength filter is configured to filter an incident IR beam in the second mode such that a partial IR beam in the second wavelength range passes through the wavelength filter.

5. A device in accordance with claim 2, wherein:
the analysis unit is configured to generate a first signal depending on a measured value of the first IR detector;
the analysis unit is configured to generate a second signal depending on a measured value of the second IR detector;
both the first signal and the second signal represent an indicator each of an ethanol content in a gas sample in the measuring chamber; and
the analysis unit is further configured to compare the two signals with one another when deciding whether or not the gas sample in the measuring chamber contains alcohol.

6. A device in accordance with claim 5, wherein the detection device is configured such that the two signals have a same sensitivity for ethanol, but have different sensitivities for at least one other substance, which may be present in a gas sample in the measuring chamber.

7. A device in accordance with claim 2, wherein the two IR radiation sources are arranged on the two opposite walls of the measuring chamber or the two IR radiation sources are arranged at spaced locations from one another on the same wall of the measuring chamber.

8. A device in accordance with claim 2, wherein
both mirrors are configured as concave mirrors; and
a distance between the two mirrors and focal lengths of the two concave mirrors are configured such that the first IR radiation source is imaged sharply onto the first IR detector and the second IR radiation source is imaged sharply onto the second IR detector.

9. A device in accordance with claim 2, wherein the opposite walls accommodate the two IR radiation sources.

10. A device in accordance with claim 2, wherein:
the device is configured to fill the measuring chamber with a gas sample that is free of alcohol and to trigger the following steps:
emitting, with each IR radiation source, a respective IR beam into the measuring chamber filled with the alcohol-free gas sample; and
each IR detector generates a respective zero measured value depending on an IR beam occurring in the case of the alcohol-free gas sample;
the analysis unit is configured to make a decision on a gas sample to be tested for alcohol in the measuring chamber:
as a function of measured values that have been generated by the two IR detectors while the measuring chamber is filled with the gas sample to be tested; and
in addition as a function of the two zero measured values.

11. A process for detecting alcohol in a gas sample, the process comprising the steps of:
providing a detection device, which comprises a measuring chamber for receiving a gas sample, a concave mirror arranged on each of two opposite walls of the measuring chamber to provide a plurality of concave mirrors, a first IR radiation source, a second IR radiation source, a first IR detector, a second IR detector, and a signal-processing analysis unit the analysis unit configured to automatically decide whether or not a gas sample in the measuring chamber contains alcohol based on measured values that have been generated by the two IR detectors, while a gas sample to be tested is present in the measuring chamber, the first IR radiation source and the second IR radiation source being arranged on one of the walls of the measuring chamber;

introducing a gas sample to be tested for alcohol into the measuring chamber, wherein the gas sample is a breath sample exhaled by a test subject;

emitting, with each of the two IR radiation sources, a respective IR beam into the measuring chamber while the gas sample to be tested is present in the measuring chamber;

passing an IR beam from the first IR radiation source through the measuring chamber such that the first IR radiation source reaches the first IR detector after the IR beam is deflected two or more times via the plurality of concave mirrors;

passing an IR beam from the second IR radiation source through the measuring chamber such that the second IR radiation source reaches the second IR detector after the IR beam is deflected two or more times via the plurality of concave mirrors;

generating, with each IR detector, at least one measured value depending on an incident IR beam while the gas sample to be tested is present in the measuring chamber;

automatically deciding, with the analysis unit, whether or not the gas sample in the measuring chamber contains alcohol, and the decision is made with the use of at least two measured values from the two IR detectors.

12. A process in accordance with claim 11, wherein the process further comprises the steps of:
    filling the measuring chamber with a gas sample that is free from alcohol;
    emitting a respective IR beam by each IR radiation source into the measuring chamber while the measuring chamber is filled with the alcohol-free gas sample;
    generating at least one zero measured value by each IR detector, always as a function of an incident IR beam, while the measuring chamber is filled with the alcohol-free gas sample; and
    the step of automatically deciding is made additionally with the use of the two zero measured values.

13. A process in accordance with claim 12, wherein the process is carried out one after another for at least two different gas samples to be tested for alcohol, and before or after the steps of introducing the gas sample and emitting the IR beams and generating the measured values while the gas sample to be tested is present in the measuring chamber, the following steps are carried out:
    the alcohol-free gas sample is introduced into the measuring chamber; and
    the IR beams are emitted and the zero measured values are generated while the alcohol-free gas sample is present in the measuring chamber, wherein the decision on whether or not the gas sample contains alcohol is made for each gas sample with the use:
    of measured values that were generated while this gas sample was present in the measuring chamber; and
    of two zero measured values from the two IR detector.

14. A process in accordance with claim 11, wherein:
    the step of deciding whether or not the gas sample in the measuring chamber contains alcohol is carried out with the use of measured values of the two IR detectors and additionally with the use of a respective calibration factor for the two IR detectors;
    the two calibration factors are generated automatically before the gas sample to be tested for alcohol is introduced into the measuring chamber; and
    the generation of the two calibration factors comprises the following steps:
    filling the measuring chamber with a gas sample, which contains ethanol; and
    generating the two calibration factors such that the two IR detectors have a same sensitivity for ethanol in the case of this alcohol-containing gas sample.

15. A device for detecting alcohol in a gas sample, the device comprising:
    a housing comprising a measuring chamber, a first wall and a second wall, the first wall being opposite the second wall;
    a first concave mirror in contact with the first wall;
    a second concave mirror located opposite the first concave mirror, the second concave mirror being in contact with the second wall, the first concave mirror and the second concave mirror defining at least a portion of the measuring chamber for receiving gas sample;
    a first IR radiation source configured to emit an IR beam into the measuring chamber;
    a second IR radiation source configured to emit an IR beam into the measuring chamber, the first IR radiation source and the second IR radiation source being arranged on the housing;
    a first IR detector configured to generate at least one measured value depending on an incident IR beam;
    a second IR detector configured to generate at least one measured value depending on an incident IR beam; and
    a signal-processing analysis unit, wherein:
        an IR beam from the first IR radiation source passes through the measuring chamber and reaches the first IR detector;
        an IR beam from the second IR radiation source passes through the measuring chamber and reaches the second IR detector; and
        the analysis unit is configured to automatically decide whether or not a gas sample in the measuring chamber contains alcohol based on measured values that have been generated by the two IR detectors, while a gas sample to be tested is present in the measuring chamber.

16. A device in accordance with claim 2, wherein the first IR detector is located adjacent to the first mirror, the second IR detector being located adjacent to the second mirror, each of the first mirror and the second mirror comprising a concave mirror surface.

17. A device in accordance with claim 16, wherein the first IR radiation source is located opposite the first IR detector, the second IR radiation source being located opposite second IR detector.

18. A device in accordance with claim 17, wherein the IR beam from the first IR radiation source is reflected two or more times via the first mirror and the second mirror prior to reaching the first IR detector, the IR beam from the second IR radiation source being reflected at least a plurality of times via the first mirror and the second mirror prior to reaching the second IR detector.

19. A device in accordance with claim 2, wherein the first IR radiation source is arranged on one of the two opposite walls of the measuring chamber, the second IR radiation source being arranged on another one of the two opposite walls of the measuring chamber, each of the first mirror and the second mirror being a concave mirror.

20. A device in accordance with claim 19, wherein the IR beam emitted by the first IR radiation source is reflected by the first mirror and the second mirror three or more times before the IR beam emitted by the first IR radiation source reaches the first IR detector, the IR beam emitted by the second IR radiation source being reflected by the first mirror and the second mirror three times or more times before the IR beam emitted by the second IR radiation source reaches the second IR detector.

* * * * *